United States Patent [19]

Martin

[11] Patent Number: 5,472,432
[45] Date of Patent: * Dec. 5, 1995

[54] CATHETER HAVING ROTARY VALVES

[75] Inventor: Geoffrey S. Martin, Mississauga, Canada

[73] Assignee: Med-Pro Design, Inc., Mississauga, Canada

[*] Notice: The portion of the term of this patent subsequent to Jun. 28, 2011, has been disclaimed.

[21] Appl. No.: 264,284

[22] Filed: Jun. 23, 1994

Related U.S. Application Data

[63] Continuation of Ser. No. 860,389, Mar. 30, 1992, Pat. No. 5,324,274.

[51] Int. Cl.⁶ ........................... A61M 5/00
[52] U.S. Cl. ................. 604/248; 137/505; 604/29; 251/304
[58] Field of Search ................. 604/32, 43, 29, 604/89, 248, 280–284, 93–96, 905, 246; 137/505; 251/304, 309

[56] References Cited

U.S. PATENT DOCUMENTS

| | | | |
|---|---|---|---|
| 3,411,534 | 11/1968 | Rose | 604/32 |
| 3,434,691 | 3/1969 | Hamilton | 604/248 |
| 4,079,737 | 3/1978 | Miller | 604/248 |
| 4,576,199 | 3/1986 | Svensson | 604/248 |
| 4,595,005 | 6/1986 | Jinotti | 604/32 |
| 4,648,868 | 3/1987 | Hardwick | 604/32 |
| 4,789,000 | 12/1988 | Aslanian | 604/248 |
| 5,053,003 | 10/1991 | Dadson | 604/29 |
| 5,197,951 | 3/1993 | Mahurkar | 604/93 |
| 5,324,274 | 6/1994 | Martin | 604/248 |

*Primary Examiner*—C. Fred Rosenbaum
*Assistant Examiner*—Chalin Smith
*Attorney, Agent, or Firm*—Rogers & Scott

[57] ABSTRACT

The invention provides a dual lumen vascular access catheter having a compact connection structure free of flexible tubing and including valves providing a visual indication of the status of the valves and hence of the catheter. The catheter includes a flexible main body defining first and second lumens and extending longitudinally between proximal and distal ends, and a relatively rigid compact connection structure is coupled directly to the main body at the proximal end of the main body. The connection structure includes a housing defining the first and second channels which extend from the first and second lumens in communication with these lumens for providing flow between the lumens and external equipment. First and second valves in the housing are positioned in the respective first and second channels in fixed relationship one with the other. The valves include respective external operators for selectively opening and closing the channels as required and the operators are positioned to be clearly visible when the catheter is in use so that the catheter presents a compact external appearance when inserted in a patient and also provides ready inspection of the status of the valves and hence of the catheter for improved convenience and safety.

6 Claims, 2 Drawing Sheets

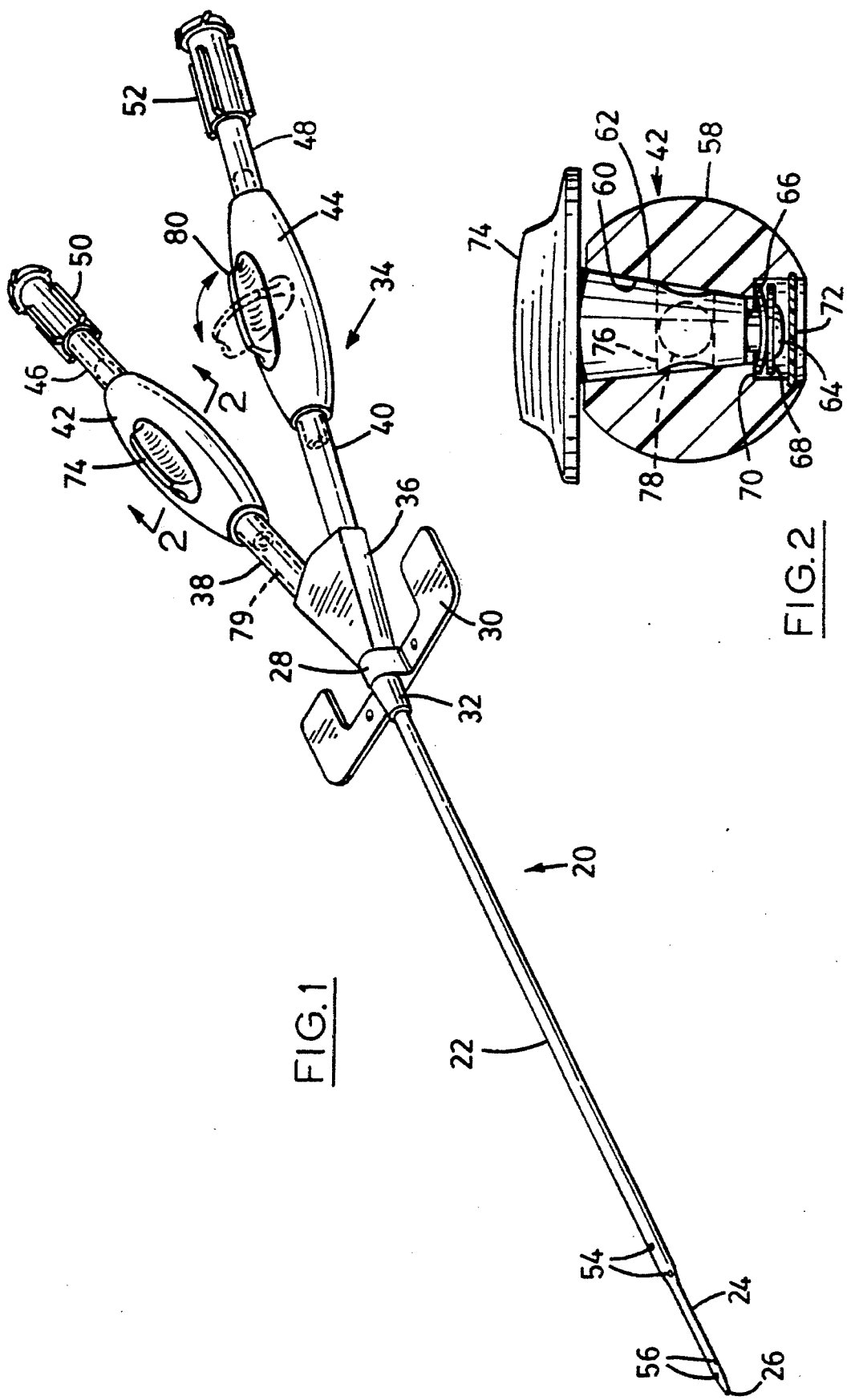

CATHETER HAVING ROTARY VALVES

This application is a continuation of application Ser. No. 07/860,389 filed on Mar. 30, 19921, now U.S. Pat. No. 5,324,274.

BACKGROUND OF THE INVENTION

This application relates to catheters used in procedures requiring intrusion into the blood circulation system of a patient, and normally referred to as vascular access catheters. More particularly, the invention relates to such catheters having a connection structure at the proximal end for controlling flow of liquids through the catheter.

FIELD OF THE INVENTION

Vascular access catheters have been developed as single lumen, dual lumen or multi-lumen catheters and are used for a variety of procedures, all of which involve intrusion into the blood circulatory system. The main body of the catheter is designed for this intrusion and the proximal or outer end includes extensions, one for each lumen. It is common practice to make these extensions from flexible tubing so that they can be manipulated outside the body and held in any convenient position using surgical dressings. Each of the tubes normally carries a luer lock connector at its free end for attachment to fluid lines and for subsequent closing and sealing of the lumens when the catheter is not in use. Because these connectors may fail, it is also common practice to place a clamp on each of the extensions so that this can be used to close the extension by deforming it and to act as a second closure.

This second line of defence is made necessary because it is possible that the luer lock and its cap may fail due to misuse or to simple flaws created during manufacture. It is evident that should the lines of defence fail while the catheter is in place, the patient is at risk of bleeding to death or suffering an air embolism if the failure is not detected very quickly.

Flexible tubes and clamps are not entirely satisfactory. The most serious problem is that the clamps close the tubes by a pinching action and if the clamp is in place for a significant length of time, it is not uncommon that the tubing will not recover when the clamp is released. The resulting crease in the tubing causes flow problems and in extreme cases the catheter has to be removed because the tube is no longer patent. The problem is most prevalent on catheters that have thermoplastic tubular extensions made from polyurethane (PU). Also the problem is exacerbated by the fact that the tubular extensions are attacked in a mild way by organic solvents such as alcohol that is always present in heparin, the anti-coagulant drug of choice used in catheters to maintain the patency of the catheter when not in use.

An alternative to PU is silicone rubber which is not attacked by solvents such as alcohol. Consequently the walls will not stick to one another, and this combined with the good rebound properties, make it suitable for use as extension tubes. Although some manufacturers use silicone rubber extensions for this reason, there is a secondary problem which has resulted in silicone rubber being superseded by PU. The problem relates to the fact that silicone is not thermoplastic and does not bond readily. Consequently if silicone rubber is to be used the tubes must be engaged using a friction fit alone and of course such a fit is subject to disconnection and adds another risk factor to the use of the catheter. It is therefore most common to use PU extensions which are permanently bonded to the remainder of the catheter.

There are other problems associated with the use of clamps. It has been found that unless they are aligned accurately before they are engaged, they can be disengaged by a minor impact and it will not be evident that the clamps have become disengaged. It would also be advantageous to reduce to size of structure to be secured to the patient at the intrusion site.

Accordingly vascular access catheters should include a structure for opening and closing the flow through the catheter which is compact, reliable, maintains patency regardless of the time during which the catheter is not in use, and which provides a clear visual indication of whether or not the catheter is open or closed.

SUMMARY OF THE INVENTION

In one of its aspects, the invention provides a dual lumen vascular access catheter having a compact connection structure free of flexible tubing and including valves providing a visual indication of the status of the valves and hence the catheter. The catheter includes a flexible main body defining first and second lumens and extending longitudinally between proximal and distal ends, and a relatively rigid compact connection structure is coupled directly to the main body at the proximal end of the main body. The connection structure includes a housing defining first and second channels which extend from the first and second lumens in communication with these lumens for providing flow between the lumens and external equipment. First and second valves in the housing are positioned in the respective first and second channels in fixed relationship one with the other. The valves include respective external operators for selectively opening and closing the channels as required and the operators are positioned to be clearly visible when the catheter is in use so that the catheter presents a compact external appearance when inserted in a patient and also provides ready inspection of the status of the valves and hence of the catheter for improved convenience and safety.

This and other aspects of the invention will be better understood with reference to the following drawings.

BRIEF DESCRIPTION OF THE DRAWINGS

FIG. 1 is an isometric view of a catheter to illustrate the use of rotary valves in a proximal end structure;

FIG. 2 is a sectional view of line 2—2 of FIG. 1;

DESCRIPTION OF THE PREFERRED EMBODIMENTS

Figure 5:
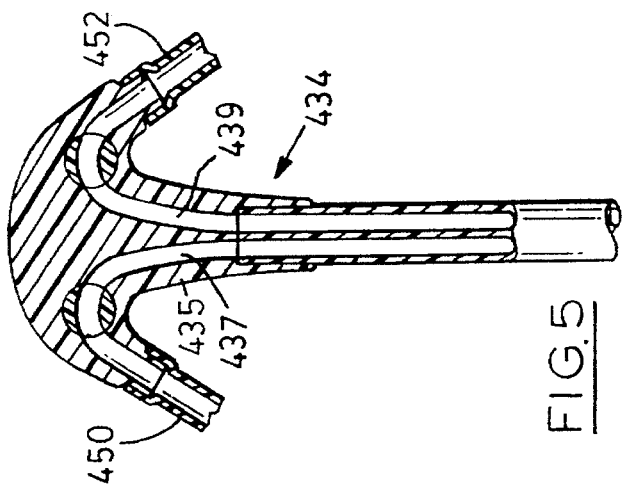
FIG. 5 is a sectional view of the structure shown in FIG. 4 to illustrate internal structure.

Reference is made firstly to FIG. 1 which illustrates a dual lumen vascular access catheter designated generally by the numeral 20 and including a main body 22 having a tip 24 at and adjacent a distal end 26. The main body 22 terminates at a proximal end 28 adjacent a conventional suture wing structure 30 rotatably mounted on the main body 22 and retained in place by a collar 32 and by an end of proximal end connection structure designated generally by the numeral 34. This connection structure consists of a lumen connector 36, intermediate flexible tubes 38, 40 which lead to respective rotary valves 42, 44 and which in turn lead to tubes 46, 48 attached to respective luer connectors 50, 52.

The lumen connector 36 forms the transition between the dual lumens in the main body 22 and the intermediate flexible tubes 38, 40. The main body could have the lumens in a side-by-side arrangement or be coaxial. In both instances, the lumens are separated for continuous flow between the respective tubes 38, 40 and the independent lumens. One lumen will project to the distal end 26 and is normally the return lumen and the other lumen is the intake lumen and will originate at openings 54 providing entry to the catheter. Flow will proceed through the lumen connector 36 and then by way of tube 40 and other parts. The return flow is through the luer connector 50 and passes eventually through the lumen connector 36 on its way to the distal end 26 and associated openings 56.

The rotary valves 42, 44 are identical in structure but could be colour coded as is conventional to show intake and outlet lumens. As better seen in FIG. 2, the rotary valve 42 includes a housing 58 defining a conical opening 60 which contains a conical shaft 62. This shaft has an extension 64 on which is mounted a spring washer 66 and a flat washer 68. The flat washer is a friction fit on the extension 64 and the spring washer biases the shaft 62 into the opening 60 to seal these two parts one against the other. The washers are contained in a cavity 70 which is conveniently sealed by a thin disk 72 which is a snap fit in a groove in the cavity.

At its upper extremity the shaft 62 has a transverse bar or operator 74 attached to the shaft and providing a small clearance with the housing 58 so that the bar does not interfere with the biasing forces created by the spring washer 66 to seat the shaft in the opening 60. The bar 74 permits the user to rotate the bar and the shaft which brings an opening 76 in the shaft 62 into alignment with a similar opening 78 in the housing 58. The opening 78 forms part of a continuous channel 79 extending from the main body (FIG. 1) to the luer connector 50. The channel is connected in the lumen connector 36 to an appropriate one of the lumens in the main body 22 as previously mentioned. A similar channel exists in tube 40 and associated parts.

As seen in FIG. 1, the bar 74 is in alignment with the channel 79 (FIG. 2) formed in the structure and closes the channel. The bar can be rotated as indicated in ghost outline with reference to the rotary valve 44 to bring the openings 76 and 78 (FIG. 2) into alignment for continuity of the channel. This permits opening and closing of the channel as required for flow through the catheter.

The materials used in manufacturing the proximal end connection structure 34 are compatible for bonding one to another either by the direct use of heat of by the use of solvents. Suitable materials would include polyvinylchloride (PVC) or polycarbonate.

The structure shown in FIG. 1 has advantages in particular types of use where some flexibility is required. It is common to use a femoral, jugular, or subclavian intrusions and because of the requirements of the patient, different methods of attachment and different forms of catheters will be appropriate. In the structure shown in FIG. 1 the flexibility provided in the intermediate flexible tubes 38, 40 will permit the catheter to be taped in position with the limitation that the connection structure 34 extends generally in the direction of the main body 22. Consequently it must be attached by first suturing the structure to the patient using the wing structure 30, and then tapes and dressings would be used to attach some of the remaining structure to the patient leaving the bar 74 and its equivalent 80 available for use. One of the advantages of the structure shown in FIG. 1 is that the flexibility in the tubes 38, 40 will permit the valves to be attached independently. However this structure is no more compact than prior art structures using clamps. It will be evident that if the overall size of the connection structure can be reduced, there will be no need to provide flexibility because the structure could be attached immediately adjacent the intrusion site without causing significant inconvenience.

Figure 3:
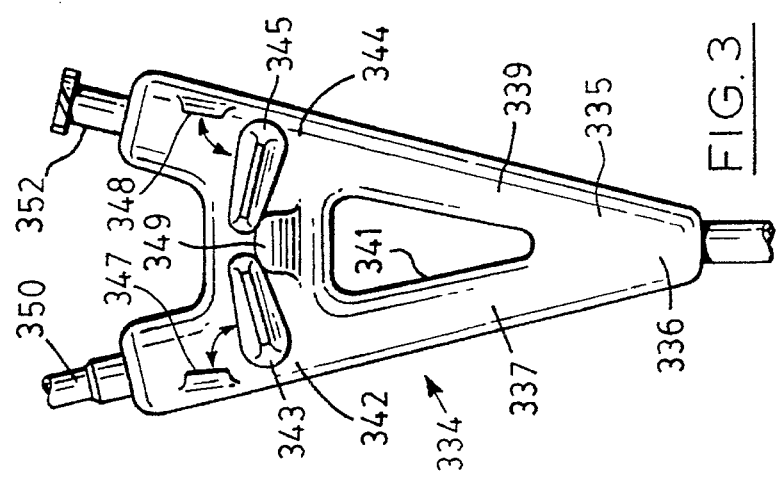
FIG. 3 is a front view of a proximal end structure of a preferred embodiment of catheter according to the invention and including a single housing for a pair of rotary valves.

Accordingly a preferred embodiment providing these attributes is to be seen in FIG. 3 where connection structure 334 is arranged with a direct connection between the valves to give a reduced overall size. In this arrangement the unitary structure dispenses with the use of flexible tubes such as 38 and 40 shown in FIG. 1. Here there is a housing 335 forming an integral lumen connector 336 which widens as it extends to a pair of diverging channel sections 337, 339 which separate about an opening 341 provided to lighten the structure. These sections meet rotary valves 342, 344 formed in the housing and having operators in the form of bars or levers 343, 345 such as those shown in FIG. 3. Stops 347, 348 are provided on the housing to ensure proper location when the valves are open and a common stop 349 locates the levers when the valves are closed. As seen in FIG. 3, the structure 334 widens as it extends from the main body of the catheter. The material used for the moulded housing 335 can provide some flexibility near the main body and this is enhanced by the weakness caused by opening 341. As a result the structure 334 will accommodate some bending for better compliance with the contours found at the insertion site.

Two forms of connections are shown in FIG. 3, the first being a simple tube 350 which corresponds to that previously described, and the other being an integral luer connector 352.

Figure 4:
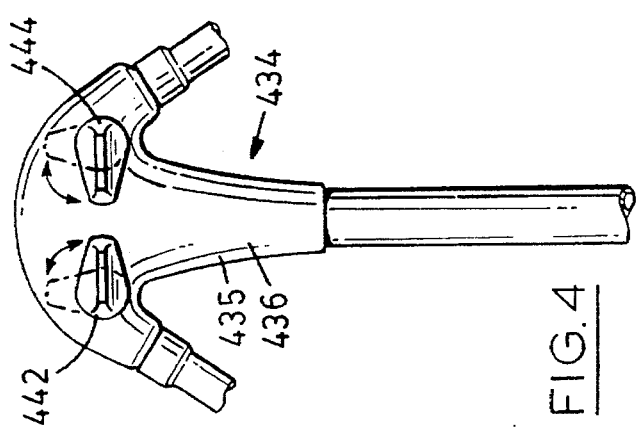
FIG. 4 is a view similar to FIG. 3 and showing a second embodiment of proximal end structure also having a single housing for a pair of rotary valves.

Another form of unitary connection structure is indicated at 434 in FIGS. 4 and 5. Here the connection structure 434 includes an integral lumen connector 436 including a housing 435 leading to curved channels 437 and 439 which pass rotary valves 442 and 444. The curved channels terminate at tubular extensions 450, 452 but could of course be arranged with luer connectors such as 352 shown in FIG. 3. The rotary valves are equipped with levers in the fashion of those shown in FIG. 3 and the diverging tubes 450, 452 can be arranged with any angle depending upon the molding shape selected. This arrangement has particular advantage where it is necessary to bring the tubes 450, 452 more or less back in the direction of the main body. Of course luer connectors could be substituted for these tubes.

Figure 6:
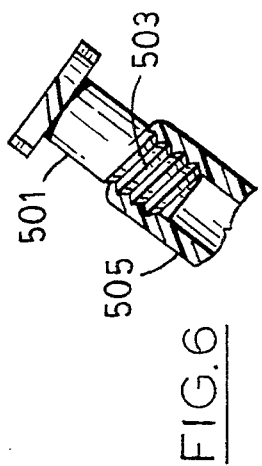
FIG. 6 is a sectional view of a portion of an embodiment illustrating a screw-in luer connector usable in all of the embodiments.

FIG. 6 is a sectional view of a form of luer connector which can be used with this structure. Instead of having fixed luer connectors, the connector 501 has a left-handed thread 503 for engagement in a housing 505 forming part of a connection structure. Consequently if the luer connector should be defective in any way, it can be removed by threading it out of the connection structure and replacing it with another luer connector. This helps to enhance the efficiency of the catheter because it is no longer necessary to remove the whole catheter in order to replace the luer connector.

The arrangements shown in FIGS. 3 and 4 would be attached so that the valve levers are outermost with the connection structure lying against the patient's skin. This is achieved because the valves are side-by-side and the exposed front face of the connection structure will show the positions of the valves even when viewed casually. Also, the structure is compact and convenient and yet the valves are readily accessible for manipulation.

It will be evident that a great variety of embodiments are possible within the limitations of the invention as claimed and all such embodiments are incorporated in this invention.

I claim:

1. A dual lumen vascular access catheter having a compact connection structure free of flexible tubing and including valves providing a visual indication of the status of the valves and hence the catheter comprising:

a flexible main body defining first and second lumens and extending longitudinally between proximal and distal ends; and a relatively rigid compact connection structure coupled directly to the main body at the proximal end of the main body, the connection structure including a housing defining first and second channels extending from the respective first and second lumens in communication with the respective lumens for providing flow between the lumens and external equipment, first and second valves in the housing and positioned in the respective first and second channels in fixed relationship one with the other, the valves including respectively external operators for selectively opening and closing the channels as required, the operators being positioned to be dearly visible when the catheter is in use whereby the catheter presents a compact external appearance when inserted in a patient and provides ready inspection of the status of the valves and hence the catheter for improved convenience and safety.

2. A dual lumen catheter as claimed in claim 1 in which the operators are moveable angularly to open and close the valves.

3. A dual lumen catheter as claimed in claim 1 in which the valves are rotary valves rotatable about respective axes arranged in parallel.

4. A dual lumen catheter as claimed in claim 1 in which the channels are curved in a common plane as they extend away from the main body.

5. A catheter having a compact connection structure free of flexible tubing, the catheter comprising:

a flexible main body defining a pair of lumens extending axially from a proximal end of the main body; a relatively rigid connection structure having a housing defining a pair of channels in communication with respective ones of the lumens; and a pair of rotary valves in the housing positioned one in each of the channels for opening and closing the channels, the valves being in fixed relationship one with the other in the housing and including exposed operators visible for inspection to indicate the positions relative to the channels and hence the status of the catheter, whereby a catheter is provided having a compact external appearance when inserted in a patient and providing for ready inspection of the status of the valves and hence the catheter for improved convenience and safety.

6. A catheter as claimed in claim 5 in which the channels are curved in a common plane as they extend away from the main body.

* * * * *